(12) United States Patent
McKinlay et al.

(10) Patent No.: US 11,859,231 B2
(45) Date of Patent: *Jan. 2, 2024

(54) MULTILAYER ELECTROCHEMICAL ANALYTE SENSORS AND METHODS FOR MAKING AND USING THEM

(71) Applicant: Medtronic MiniMed, Inc., Northridge, CA (US)

(72) Inventors: Robert McKinlay, West Hills, CA (US); Tri T. Dang, Winnetka, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 98 days.

This patent is subject to a terminal disclaimer.

(21) Appl. No.: 17/528,496

(22) Filed: Nov. 17, 2021

(65) Prior Publication Data
US 2022/0073961 A1    Mar. 10, 2022

Related U.S. Application Data

(63) Continuation of application No. 15/891,264, filed on Feb. 7, 2018, now Pat. No. 11,186,859.

(51) Int. Cl.
*C12Q 1/00* (2006.01)
*G01N 27/327* (2006.01)
*A61B 5/1486* (2006.01)
*A61B 5/145* (2006.01)
*A61B 5/00* (2006.01)

(52) U.S. Cl.
CPC ............ *C12Q 1/006* (2013.01); *A61B 5/1486* (2013.01); *A61B 5/14532* (2013.01); *A61B 5/14865* (2013.01); *A61B 5/6849* (2013.01); *G01N 27/3271* (2013.01); *A61B 5/1451* (2013.01);

(Continued)

(58) Field of Classification Search
CPC ...... G01N 27/48; G01N 27/26; G01N 27/327; G01N 27/10; G01N 27/06; G01N 27/3272; G01N 27/40; G01N 27/3271; C12Q 1/00; C12Q 1/02; C12Q 1/006; C12Q 1/34; C12Q 1/54; A61B 5/14532; A61B 5/05; A61B 5/1486; A61B 5/14865; A61B 2562/12

See application file for complete search history.

(56) References Cited

U.S. PATENT DOCUMENTS 4,755,173 A    7/1988 Konopka et al.
5,391,250 A    2/1995 Cheney, II et al.
(Continued)

FOREIGN PATENT DOCUMENTS

EP    3078750    1/2018
WO    2014025430    2/2014

OTHER PUBLICATIONS

European Communication dated Nov. 23, 2022 for EP Application No. 19720716.0.

(Continued)

*Primary Examiner* — Gurpreet Kaur
(74) *Attorney, Agent, or Firm* — GATES & COOPER LLP

(57) ABSTRACT

Embodiments of the invention provide multilayer analyte sensors having material layers (e.g. high-density amine layers) and/or configurations of material layers that function to enhance sensor function, as well as methods for making and using such sensors. Typical embodiments of the invention include glucose sensors used in the management of diabetes.

20 Claims, 9 Drawing Sheets

(52) U.S. Cl.
CPC ...... *A61B 2562/12* (2013.01); *G01N 27/3272* (2013.01)

(56) References Cited

U.S. PATENT DOCUMENTS

| | | | |
|---|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 11,186,859 B2 * | 11/2021 | McKinlay .......... A61B 5/14865 |
| 2007/0123819 A1 | 5/2007 | Mernoe et al. |
| 2009/0018426 A1 | 1/2009 | Markle et al. |
| 2009/0101498 A1 | 4/2009 | Papadimitrakopoulos et al. |
| 2010/0160861 A1 | 6/2010 | Causey, III et al. |
| 2011/0082356 A1 | 4/2011 | Yang et al. |
| 2011/0152654 A1 | 6/2011 | Wang et al. |
| 2011/0168576 A1 | 7/2011 | Kampouris et al. |
| 2014/0012115 A1 | 1/2014 | Li et al. |

OTHER PUBLICATIONS

PCT International Search Report & Written Opinion dated Jul. 5, 2019 for PCT Application No. PCT/US2019/016525.

Tang, W., et al., "Glucose Biosensor Based on a Glassy Carbon Electrode Modified with Polythionine and Multiwalled Carbon Nanotubes", PLOS One, May 2014, pp. 1-8, vol. 9, No. 5.

Non-Final Office Action dated Apr. 15, 2020 for U.S. Appl. No. 15/891,264.

* cited by examiner $R^1$ = Alkyl functional groups of various chain lengths (linear and/or branc $R^2$ = Ketone functional group $R^3$ = Nitrogen functional group

MULTILAYER ELECTROCHEMICAL ANALYTE SENSORS AND METHODS FOR MAKING AND USING THEM

CROSS REFERENCE TO RELATED APPLICATIONS

This application is a continuation application that claims the benefit under 35 U.S.C. 120 of U.S. patent application Ser. No. 15/891,264, filed Feb. 7, 2018, the contents of which are incorporated herein by reference.

TECHNICAL FIELD

The present invention relates to methods and materials useful for analyte sensor systems, such as glucose sensors used in the management of diabetes.

BACKGROUND OF THE INVENTION

Sensors are used to monitor a wide variety of compounds in various environments, including in vivo analytes. The quantitative determination of analytes in humans is of great importance in the diagnoses and maintenance of a number of pathological conditions. Illustrative analytes that are commonly monitored in a large number of individuals include glucose, lactate, cholesterol, and bilirubin. The determination of glucose concentrations in body fluids is of particular importance to diabetic individuals, individuals who must frequently check glucose levels in their body fluids to regulate the glucose intake in their diets. The results of such tests can be crucial in determining what, if any, insulin and/or other medication need to be administered.

Analyte sensors typically include components that convert interactions with analytes into detectable signals that can be correlated with the concentrations of the analyte. For example, some glucose sensors use amperometric means to monitor glucose in vivo. Such amperometric glucose sensors typically incorporate electrodes coated with glucose oxidase, an enzyme that catalyzes the reaction between glucose and oxygen to yield gluconic acid and hydrogen peroxide ($H_2O_2$). The $H_2O_2$ formed in this reaction alters an electrode current to form a detectable and measurable signal. Based on the signal, the concentration of glucose in the individual can then be measured.

A typical electrochemical glucose sensor works according to the following chemical reactions:

$$\text{GLUCOSE} + O_2 \xrightarrow{\text{GLUCOSE OXIDASE}} \text{GLUCONIC ACID} + H_2O_2 \quad \text{Equation 1}$$

$$H_2O_2 \rightarrow O_2 + 2H^+ + 2e^- \quad \text{Equation 2}$$

The glucose oxidase is used to catalyze the reaction between glucose and oxygen to yield gluconic acid and hydrogen peroxide as shown in equation 1. The $H_2O_2$ reacts electrochemically as shown in equation 2, and the current is measured by a potentiostat. The stoichiometry of the reaction provides challenges to developing in vivo sensors. In particular, for optimal glucose oxidase based sensor performance, sensor signal output should be determined only by the analyte of interest (glucose), and not by any co-substrates ($O_2$) or kinetically controlled parameters such as diffusion. If oxygen and glucose are present in equimolar concentrations, then the $H_2O_2$ is stoichiometrically related to the amount of glucose that reacts with the glucose oxidase enzyme; and the associated current that generates the sensor signal is proportional to the amount of glucose that reacts with the enzyme. If, however, there is insufficient oxygen for all of the glucose to react with the enzyme, then the current will be proportional to the oxygen concentration, not the glucose concentration. Consequently, for a glucose sensor to provide a signal that depends solely on the concentrations of glucose, glucose must be the limiting reagent, i. e. the $O_2$ concentration must be in excess for all potential glucose concentrations. A problem with using such glucose sensors in vivo, however, is that the oxygen concentration where the sensor is implanted in vivo is low relative to glucose, a phenomenon which can compromise the accuracy of glucose sensor readings (and consequently, this phenomenon is termed the "oxygen deficit problem").

Important components of certain electrochemical analyte sensors include the layers of material that are disposed over the electrodes in order allow the sensor to appropriately measure analyte signals in view of issues such as the oxygen deficit problem discussed above. Based on various factors such as the material compositions used in layered electrochemical sensor stacks as well as where these compositions are disposed within the stack architecture, a sensor may vary in terms of its stability, reliability, and sensitivity in detecting analyte signals. In this context, there is a need in the art for multilayer electrochemical sensors having layered materials that are optimized for sensor production and function. There is also a need for multilayer electrochemical sensors having improved stability, reliability, and sensitivity in detecting analyte signals. Embodiments of the invention disclosed herein meet these as well as other needs.

SUMMARY OF THE INVENTION

Embodiments of the invention disclosed herein provide electrochemical sensor designs that include multilayer analyte sensor stacks. In these embodiments, the components of the multilayer analyte sensor stacks are formed from selected layers/materials and disposed within the stack architecture in a specific orientation that is designed to provide these sensors with enhanced functional properties. The disclosure further provides methods for making and using such sensors. As discussed in detail below, typical embodiments of the invention relate to the use of a sensor that measures a concentration of an aqueous analyte of interest or a substance indicative of the concentration or presence of the analyte in vivo (e.g. glucose sensors used in the management of diabetes). Embodiments of the invention provide innovative ways to simplify the design of certain conventional electrochemical sensors having a plurality of layers disposed over electrodes.

An illustrative embodiment of the invention is an electrochemical analyte sensor comprising a base layer, a working electrode disposed on the base layer, and a multilayer analyte sensor stack disposed upon the working electrode. In this embodiment, the multilayer analyte sensor stack comprises an analyte sensing layer (e.g. one comprising glucose oxidase) disposed directly on the working electrode, and this layer functions to detectably alter the electrical current at the working electrode in the presence of an analyte. In these embodiments, a high-density amine ("HDA") layer which comprises polymers having a plurality of repeating amine groups (e.g. poly-l-lysine polymers) is disposed directly on top of the analyte sensing layer. In these embodiments, an analyte modulating layer (e.g. one comprising a glucose limiting membrane which modulates the diffusion of glucose from interstitial fluid to the working electrode) is further disposed directly on top of this high-density amine layer.

In typical analyte sensor embodiments, the multilayer analyte sensor stack does not comprise at least one of: a further layer comprising an albumin; a further layer comprising a siloxane adhesion promoting agent; or a layer comprising glutaraldehyde. For example, in the working embodiments disclosed herein, the multilayer analyte sensor stack consists essentially of the analyte sensing layer, the high-density amine layer and the analyte modulating layer. In typical embodiments of the invention, the high-density amine layer comprises a first side in direct contact with the analyte sensing layer, and a second side in direct contact with the analyte modulating layer and this high density amine layer functions as an adhesive layer that binds the analyte sensing layer to the analyte modulating layer. Optionally, the analyte sensing layer comprises glucose oxidase disposed in the layer so that the analyte sensor senses glucose; and the high-density amine layer further functions to decrease sensor signal changes that result from fluctuating levels of oxygen ($O_2$). In illustrative working embodiments of the invention disclosed herein, the polymers having a plurality of repeating amine groups that are used to form the high density amine layer comprise poly-l-lysine polymers having molecular weights between 30 KDa and 300 KDa, for example, molecular weights between 150 KDa and 300 KDa. Typically, the polymers having a plurality of repeating amine groups in the high-density amine layer are in amounts from 0.1 weight-to-weight percent to 0.5 weight-to-weight percent. Optionally, the high-density amine layer is from 0.1 to 0.4 microns thick.

Another embodiment of the invention is a method of making an electrochemical analyte sensor comprising the steps of: disposing a working electrode on a base layer; disposing an analyte sensing layer (e.g. one comprising glucose oxidase) over the working electrode. These methods further comprise disposing a high-density amine layer comprising polymers having a plurality of repeating amine groups (e.g. poly-l-lysine polymers) directly on the analyte sensing layer (e.g. using a spray or spin coating process); and disposing an analyte modulating layer (e.g. a glucose limiting membrane) directly on the high-density amine layer. Optionally, the electrochemical sensor comprises a multilayer analyte sensor stack disposed over the working electrode, said multilayer analyte sensor stack consisting essentially of the analyte sensor layer, the high-density amine layer and the analyte modulating layer. In the working embodiments disclosed herein, the analyte sensing layer comprises glucose oxidase disposed in the layer so that the analyte sensor senses glucose; and the high-density amine layer functions to decrease sensor signal changes that result from fluctuating levels of oxygen ($O_2$) during glucose sensing in vivo.

Yet another embodiment of the invention is a method of sensing glucose concentrations in a fluid (e.g. the interstitial fluid of a diabetic patient or another location where oxygen concentrations are low relative to glucose), the method comprising disposing an electrochemical glucose sensor in the fluid, wherein the electrochemical glucose sensor comprises a base layer; a working electrode disposed on the base layer; and a multilayer analyte sensor stack disposed on the working electrode. In these embodiments, the multilayer analyte sensor stack comprises an analyte sensing layer comprising glucose oxidase disposed over the working electrode that detectably alters the electrical current at the working electrode in the presence of an glucose; a high-density amine layer comprising polymers having a plurality of repeating amine groups (e.g. poly-l-lysine polymers), wherein the high-density amine layer is disposed over the analyte sensing layer; and an analyte modulating layer disposed over the high-density amine layer that comprises material that modulates the diffusion of glucose therethrough. These methods further comprise monitoring fluctuations in electrical conductivity that occur in the present of glucose; and correlating the fluctuations in electrical conductivity with a concentration of glucose so that glucose concentrations in the fluid are sensed. In such embodiments, the high-density amine layer functions to increase adhesion between the layers of the multilayer analyte sensor stack while simultaneously decreasing sensor signal changes that result from fluctuating levels of oxygen ($O_2$) as glucose concentrations in the fluid are sensed.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

As shown in FIG. 4, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

FIG. 2A). Data from this study shows to effectiveness of glucose sensors having HDA polymer layers that, for example, function as adhesion promoters etc. in electrochemical analyte sensors having multilayer sensor stacks.

DETAILED DESCRIPTION OF THE INVENTION

Figure 1:
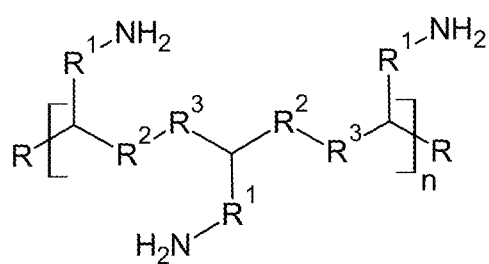
FIG. 1 provides a schematic that illustrates the general structure of high-density amine (HDA) polymer units that can be used to make high-density amine polymers. R1 comprises alkyl functional groups, for example those comprising between 1-20 carbon atoms. R2 comprises ketone functional groups, for example those comprising at least one oxygen atom and between 1-20 carbon atoms. R3 comprises nitrogen functional groups, for example those comprising at least one nitrogen atom and between 1-20 carbon atoms.

Unless otherwise defined, all terms of art, notations, and other scientific terms or terminology used herein are intended to have the meanings commonly understood by those of skill in the art to which this invention pertains. In some cases, terms with commonly understood meanings may be defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below.

All numbers recited in the specification and associated claims that refer to values that can be numerically characterized with a value other than a whole number (e.g. the diameter of a circular disc) are understood to be modified by the term "about". Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Furthermore, all publications mentioned herein are incorporated herein by reference to disclose and describe the methods and/or materials in connection with which the publications are cited. Publications cited herein are cited for their disclosure prior to the filing date of the present application. Nothing herein is to be construed as an admission that the inventors are not entitled to antedate the publications by virtue of an earlier priority date or prior date of invention. Further the actual publication dates may be different from those shown and require independent verification.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In common embodiments, the analyte is glucose. However, embodiments of the invention can be used with sensors designed for detecting a wide variety other analytes. Illustrative analytes include but are not limited to, lactate as well as salts, sugars, proteins fats, vitamins and hormones that naturally occur in vivo (e.g. in blood or interstitial fluids). The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor" for example in "analyte sensor," is used in its ordinary sense, including, without limitation, means used to detect a compound such as an analyte. A "sensor system" includes, for example, elements, structures and architectures (e.g. specific 3-dimensional constellations of elements) designed to facilitate sensor use and function. Sensor systems can include, for example, compositions such as a layer of material having selected properties such as a high density amine layer formed from polymers having a plurality of repeating amine groups (e.g. a high-density amine layer comprising from 0.1 weight-to-weight percent to 0.5 weight-to-weight percent poly-l-lysine having molecular weights between 150 KDa and 300 KDa), as well as electronic components such as elements and devices used in signal detection and analysis (e.g. current detectors, monitors, processors and the like).

The terms "electrochemically reactive surface" and "electroactive surface" as used herein are broad terms and are used in their ordinary sense, including, without limitation, the surface of an electrode where an electrochemical reaction takes place. In one example, a working electrode measures hydrogen peroxide produced by the enzyme catalyzed reaction of the analyte being detected, creating an electric current (for example, detection of glucose analyte utilizing glucose oxidase produces $H_2O_2$ as a byproduct, $H_2O_2$ reacts with the surface of the working electrode producing two protons ($2H^+$), two electrons ($2e^-$) and one molecule of oxygen ($O_)$ which produces the electronic current being detected). In the case of the counter electrode, a reducible species, for example, $O_2$ is reduced at the electrode surface in order to balance the current being generated by the working electrode.

As discussed in detail below, embodiments of the invention relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. The product is then measured using electrochemical methods and thus the output of an electrode system functions as a measure of the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765, 7,033,336 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042,625, and WO 03/074107, and European Patent Application EP 1153571, the contents of each of which are incorporated herein by reference.

Illustrative Embodiments of the Invention and Associated Characteristics

Embodiments of the invention disclosed herein provide sensors designed to include multilayer analyte sensor stacks formed from selected materials that provide the sensors with enhanced functional and/or material properties. The disclosure further provides methods for making and using such sensors. As discussed in detail below, typical embodiments of the invention relate to the use of a sensor that measures a concentration of an aqueous analyte of interest or a substance indicative of the concentration or presence of the analyte in vivo. In some embodiments, the sensor is a subcutaneous, intramuscular, intraperitoneal, intravascular or transdermal device. Typically, the sensor can be used for continuous analyte monitoring. The sensor embodiments disclosed herein can use any known method, including invasive, minimally invasive, and non-invasive sensing techniques, to provide an output signal indicative of the concentration of the analyte of interest. Embodiments of the invention provide an innovative way to simplify the design of conventional electrochemical sensors having a plurality of layers disposed over the working electrode.

Figure 2A:
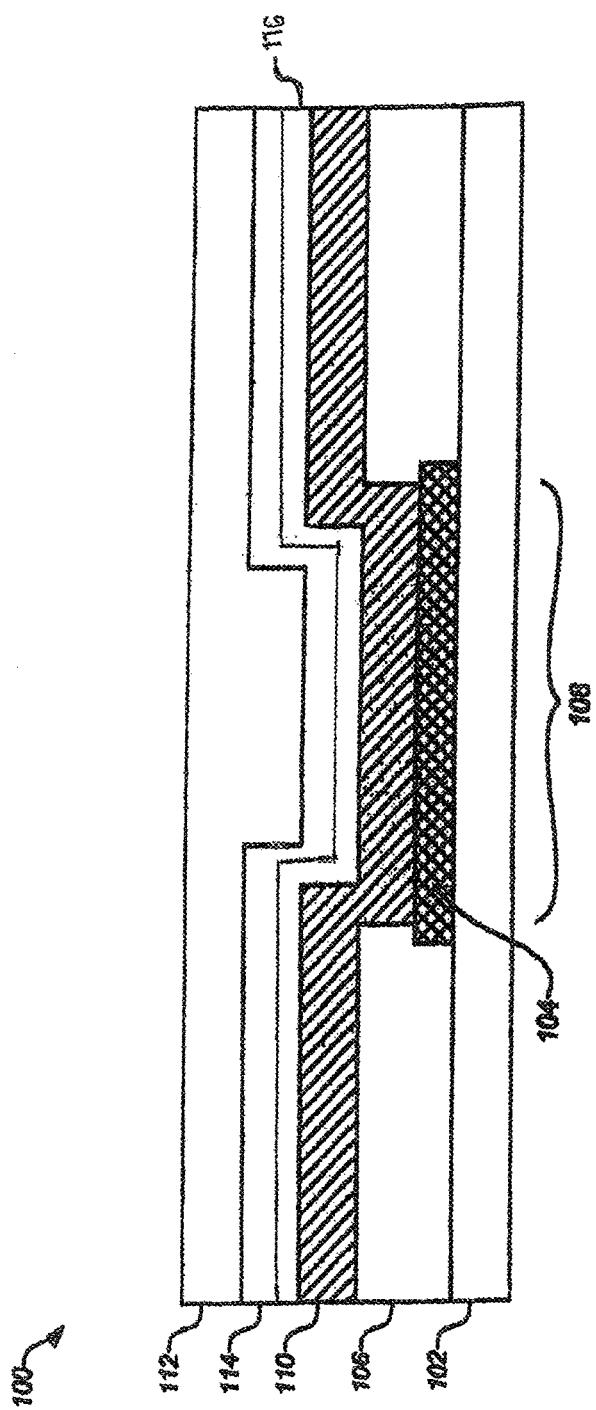
FIG. 2A provides a schematic showing a conventional (PRIOR ART) sensor design comprising an amperometric analyte sensor formed from a plurality of planar layered elements which include albumin protein layer and an adhesion promoter layer.

Embodiments of the invention having a constellation of elements including a high density amine layer exhibit a number of advantages over conventional multilayer electrochemical sensor designs (e.g. as disclosed in FIG. 2A). For example, embodiments of the invention have fewer layers of materials, a property that can be used to simplify the manufacturing process & reduce sensor-to-sensor variation as compared to conventional processes for making analyte sensor stacks, processes which utilize a multicomponent adhesive layer to "glue" GLM to GOx (where a layer is created in-situ through many simultaneous chemical reactions, resulting in sensor-to-sensor variability). See FIG. 2B for a comparison of conventional analyte sensors and the HDA sensors disclosed herein. Another advantage is that certain HDA sensor embodiments disclosed herein do not comprise Human Serum Albumin (HSA). Other advantages of embodiments of the invention include improvements in stability that come with the elimination of glutaraldehyde (glutaraldehyde cross-linked glucose oxidase in conventional sensor designs may decrease GOx activity and stability). By removing glutaraldehyde, we remove this potential cause of sensor instability. Another associated advantage is that the sensor embodiments disclosed herein are observed to exhibit more robust sterilization profile in e-beam and ETO processes.

Figure 6:
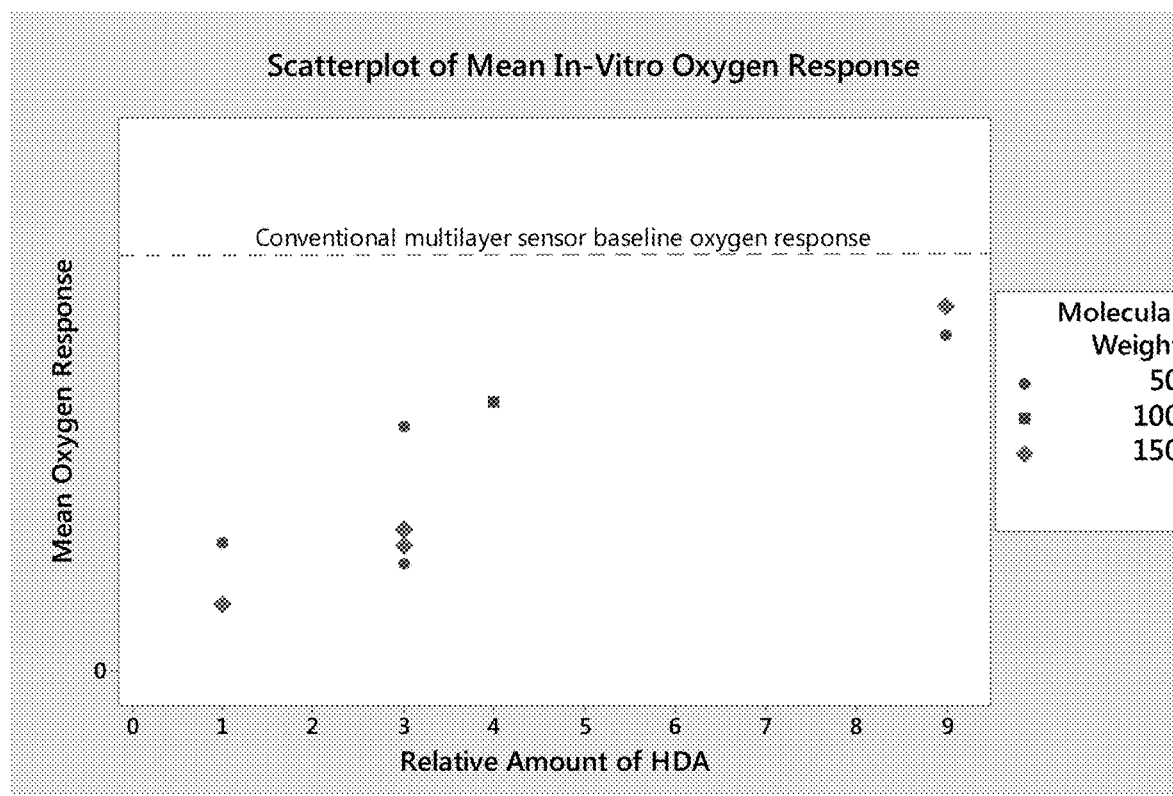
FIG. 6 is a graph of data from sensor embodiments of HDA multilayer stacks formed from poly-l-lysine having different molecular weights. This data confirms that sensor embodiments having HDA multilayer stacks have lower baseline oxygen responses as compared to sensor embodiments formed using conventional multilayer stacks.
Figure 7:
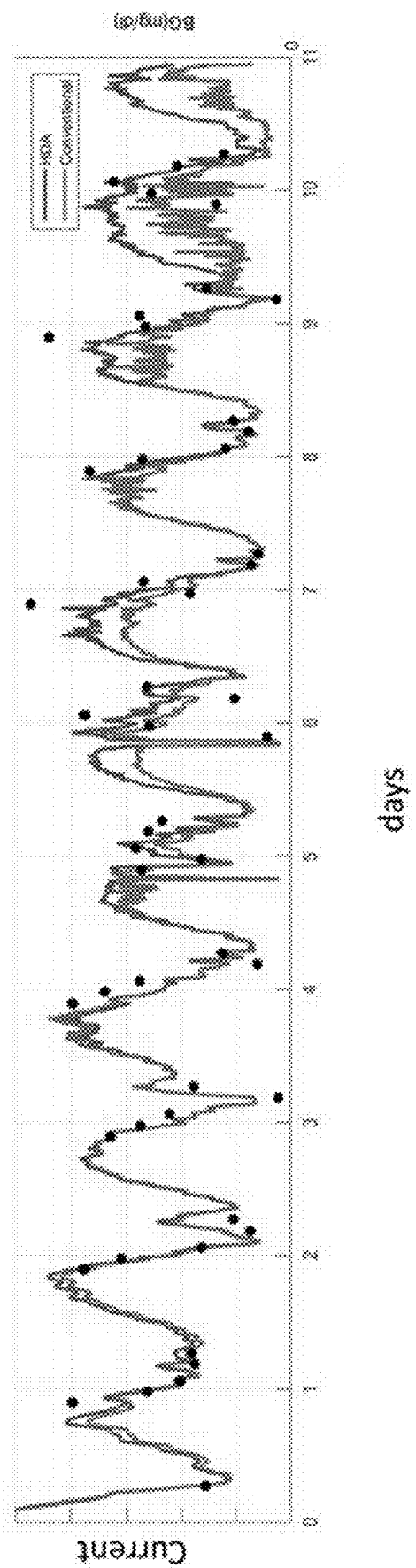
FIG. 7 shows data from an in vivo comparative study monitoring glucose in pigs using a amperometric glucose sensor comprising an HDA material layer as disclosed herein and compared to conventional sensors not having an HDA layer (e.g.
Figure 8:
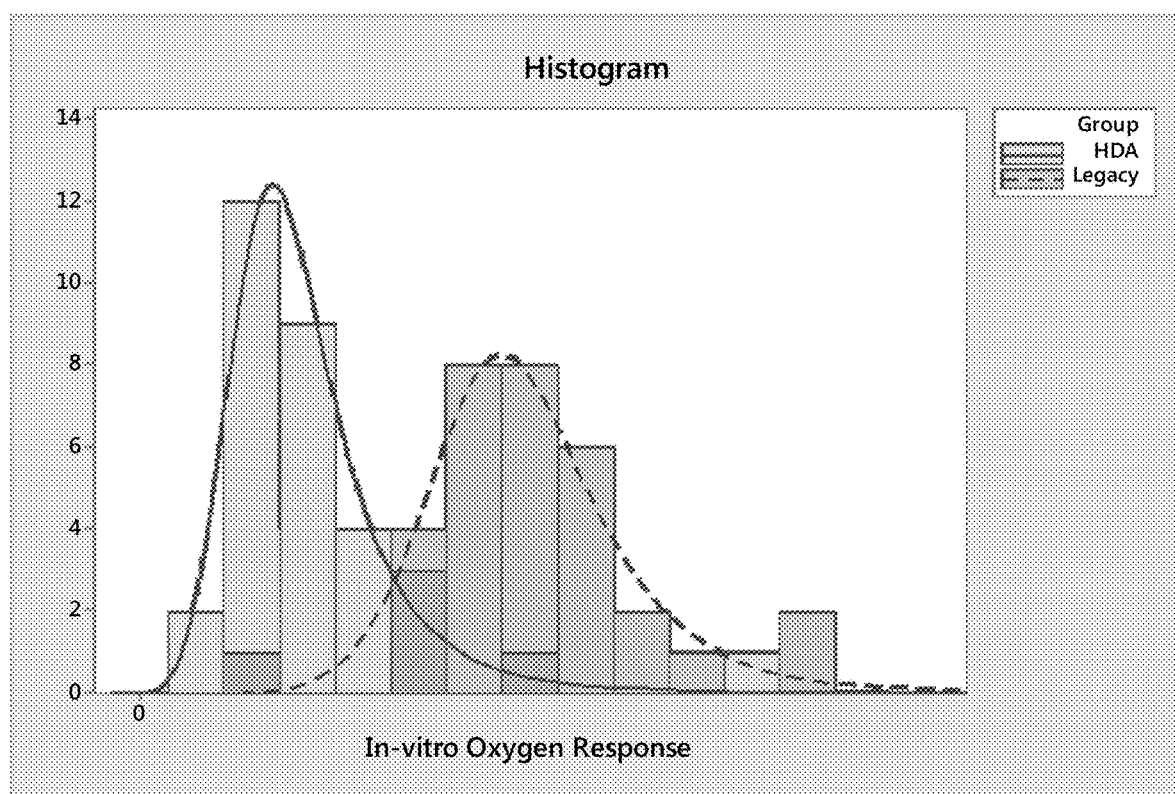
FIG. 8 shows data from an in vitro comparative study monitoring glucose sensing under different concentrations of $O_{in}$ order to compare the oxygen response in legacy/conventional glucose oxidase based sensors with amperometric glucose sensor comprising an HDA material layer as disclosed herein. These studies show that glucose sensors comprising an HDA material layer as disclosed herein display lower in-vitro signal changes to oxygen concentration changes as compared to legacy/conventional glucose oxidase based sensors.

Other associated advantages of the unique constellations of layered materials disposed over working electrode(s) that are disclosed herein include more robust layer surfaces and increased stability over arrange of different initialization profiles (sensors comprising HDA layers are stable under a range of different initialization profiles). Other advantages can include, for example, a more uniform layers as well as more sites for electrochemical reactions, features which contribute to the stability and/or sensitivity of layered sensor structures. For example, by providing smoother and more adhesive surfaces that can contribute to sensor stability by decreasing the possibility that one or more layers of material may delaminate. Importantly, a key advantage is an improved oxygen response that is observed in glucose oxidase based sensors formed with HDA layer, with HDA Poly-l-lysine sensors showing less signal changes over variable oxygen concentrations (5% to 1%). This property addresses the oxygen deficit problem with glucose sensors that is discussed above (as illustrated in data from illustrative working examples of HDA comprising sensor embodiments shown in FIGS. 6 and 8). FIG. 7 then shows data from an in vivo comparative study monitoring glucose in pigs using a amperometric glucose sensor comprising an HDA material layer as disclosed herein and compared to conventional sensors not having an HDA layer (e.g. FIG. 2A).

In the high density amine layers disclosed herein, the polymers having a plurality of repeating amine groups can adopt a variety of configurations. The simplest polymer architecture having a plurality of repeating amine groups is a linear chain: a single backbone with no branches. Alternatively, the polymer can be branched. A branched polymer molecule is composed of a main chain with one or more substituent side chains or branches. Special types of branched polymers include dendrimers. Dendrimers are a special case of macromolecules wherein every monomer unit is branched. In some embodiments of the invention, the polymers having a plurality of repeating amine groups within the HDA layer exhibit linear, and/or branched and/or dendrimer like structures. In illustrative embodiments of the invention disclosed herein, the HDA layer comprises poly-l-lysine polymers.

While the illustrative working embodiments of the invention are formed from linear polymers, the polymers having a plurality of repeating amine groups within the HDA layer can exhibit linear, branched and/or dendrimer like structures. Such HDA polymers include, for example, Poly-l-lysine, Poly-D-lysine, Chitosan, Amino-dextran, Polyethylene imine, other Poly-l-amino acid polymers and the like. In certain embodiments of the invention, polymers comprise the general structure shown below with R1, R2 and R3 where:

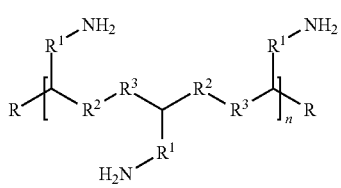

R[1]=Alkyl functional groups of various chain lengths (linear and/or brand
R[2]=Ketone functional group
R[3]=Nitrogen functional group In certain embodiments, the polymer comprises a poly-l-lysine unit:

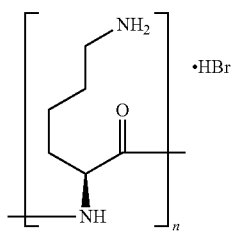

In one specific illustrative embodiment, the polymer comprises a molecular structure such as:

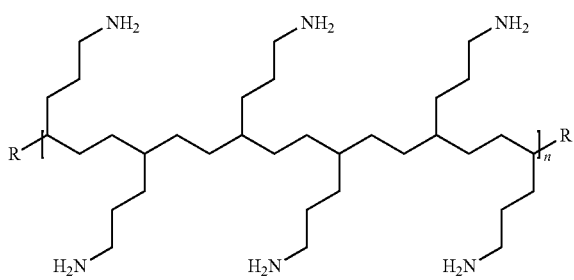

In another specific illustrative embodiment, the polymer comprises a molecular structure such as:

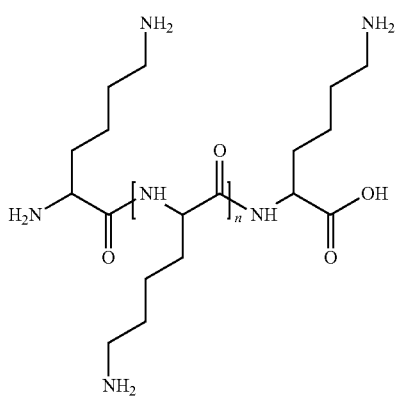

The high-density amine layer can be formed according to art accepted processes, for example by weighing out applicable amount of a polymer such as poly-l-lysine, dissolving this amount of poly-l-lysine in applicable amount of water so that a clear solution is formed and stirring for 1 hour. Artisans can then use this solution to make a concentration of 0.1 to 0.5 weight-to-weight percent (w/w %) high-density amine composition to form a layer in a sensor disclosed herein. Typically, the layer is applied to the senor stack by spraying the poly-l-lysine solution onto the substrate some number of times (e.g. 3× wherein the biodot repeats a spray cycle), so that more repeated applications=more material deposited onto the substrates. In working embodiments disclosed herein, poly-l-lysine polymers having different molecular weights were examiner, with HMW=High Molecular Weight=150 to 300 KDa, MMW=Medium Molecular Weight=70 to 150 KDa, and LMW=Low Molecular Weight=30 to 70 KDa.

An illustrative embodiment of the invention is an electrochemical analyte sensor comprising a base layer, a working electrode disposed on the base layer, and a multilayer analyte sensor stack disposed upon the working electrode. In this embodiment, the multilayer analyte sensor stack comprises an analyte sensing layer disposed directly on the working electrode, wherein the analyte sensing layer detectably alters the electrical current at the working electrode in the presence of an analyte, a high-density amine layer disposed over the analyte sensing layer, wherein the high-density amine layer comprises poly-l-lysine polymers, and an analyte modulating layer (e.g. a glucose limiting membrane) disposed over the high-density amine layer, wherein the analyte modulating layer modulates the diffusion of analyte (e.g. glucose) from an external environment (e.g. interstitial fluid) to the working electrode.

In such analyte sensor embodiments, the multilayer analyte sensor stack does not comprise at least one of: a further layer comprising an albumin (and optionally no sensor layer comprises an albumin); a further layer comprising a siloxane adhesion promoting agent; or a further layer comprising glutaraldehyde (and optionally no sensor layer is formed using glutaraldehyde or comprises glutaraldehyde moieties). For example, in the working embodiments disclosed herein, the multilayer analyte sensor stack consists essentially of the analyte sensing layer, the high-density amine layer and the analyte modulating layer. In typical embodiments of the invention, the high-density amine layer comprises a first side in direct contact with the analyte sensing layer, and a second side in direct contact with the analyte modulating layer, contact which allows this layer to function as an adhesive layer that binds the analyte sensing layer to the analyte modulating layer. Optionally, the analyte sensing layer comprises glucose oxidase disposed in the layer so that the analyte sensor senses glucose; and the high-density amine layer further functions to decrease sensor signal changes that result from fluctuating levels of $O_(see, e.g. the data from illustrative embodiments of the invention shown in FIG. 6). The polymers having a plurality of repeating amine groups within the HDA layer exhibit linear, and/or branched and/or dendrimer like structures. In certain embodiments of the invention, the poly-l-lysine in the high-density amine layer has molecular weights between 30 KDa and 300 KDa, for example, molecular weights between 150 KDa and 300 KDa. Typically, the poly-l-lysine in the high-density amine layer is in amounts from 0.1 weight-to-weight percent to 0.5 weight-to-weight percent. Optionally, the high-density amine layer is from 0.1 to 0.4 microns thick. These 0.1 to 0.4 micron thin adhesive layers have unexpected advantages in that they exhibit a lower oxygen response as well as faster hydration times as compared to conventional sensors not having such thin HDA layers.

Another embodiment of the invention is a method of making an electrochemical analyte sensor comprising the steps of: disposing a working electrode on a base layer; disposing an analyte sensing layer over the working electrode, wherein the analyte sensing layer detectably alters the electrical current at the working electrode in the presence of an analyte; disposing a high-density amine layer comprising for example HDA polymers directly on the analyte sensing layer (e.g. using a spray coating process); and disposing an analyte modulating layer directly on the high-density amine layer, wherein the analyte modulating layer modulates the diffusion of analyte therethrough so that an electrochemical analyte sensor is made. Optionally, the electrochemical sensor comprises a multilayer analyte sensor stack disposed over the working electrode, said multilayer analyte sensor stack consisting essentially of the analyte sensor layer, the high-density amine layer and the analyte modulating layer. An illustrative poly-l-lysine solution used to make an embodiment of the invention is 150 to 300 KDa poly-l-lysine, 0.3 poly-l-lysine w/w %, that is applied in approximately 2 spray repeats. In the working embodiments disclosed herein, the analyte sensing layer comprises glucose oxidase disposed in the layer so that the analyte sensor senses glucose; and the high-density amine layer functions to decrease sensor signal changes that result from fluctuating levels of oxygen ($O_2$) during glucose sensing.

One unexpected advantage of analyte sensors comprising the high-density amine layers disclosed herein is their ability to maintain excellent functionality (i.e. analyte sensing) following sterilization by Ethylene Oxide. Specifically, when devices such as analyte sensors are sterilized with ethylene oxide, problems can arise if the ethylene oxide reacts with, and inhibits the activity of one or more sensitive components of the device, such as the enzyme glucose oxidase in amperometric glucose sensors. Such problems can prevent the effective use of ethylene oxide sterilization procedures on such devices. Methods and materials designed to address such challenges in this technology (e.g. the high-density amine layers disclosed herein) are therefore desirable. In this context, embodiments of the invention include methods for making analyte sensors comprising the high-density amine layers disclosed herein which include the step of sterilizing the sensor with ethylene oxide, sensors comprising the high-density amine layers disclosed herein that have been sterilized with ethylene oxide, and methods for sensing analytes such as glucose with these sensors comprising the high-density amine layers disclosed herein that have been sterilized with ethylene oxide. A variety of ethylene oxide sterilization procedures are known in the art (see, e.g. U.S. Patent Publications 20120252125, 20110233068, 20070292305 and 20050089442, the contents of which are incorporated herein by reference). Illustrative ethylene oxide parameters are as follows.

| Parameter | Level | Units |
|---|---|---|
| Ethylene Oxide Concentration | 200-800 | mg/L |
| Humidity | >=30 | % RH |
| Temperature | <=140 | F. |
| Dwell Time | 2-12 | Hours |
| CO2 mixture | <=80% | % composition |

Figure 5:
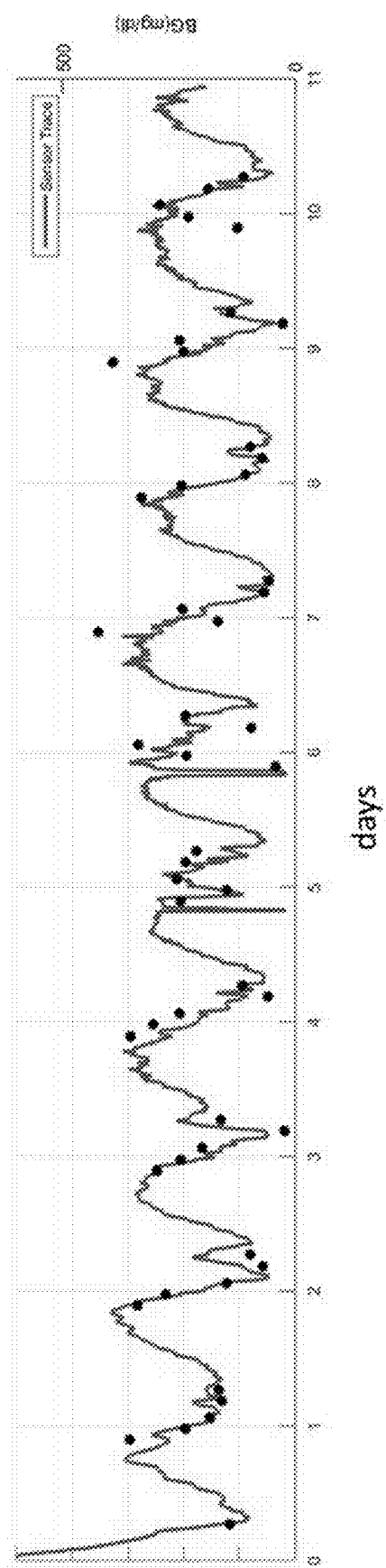
FIG. 5 shows data from an in vivo study monitoring glucose in pigs using a amperometric glucose sensor comprising an HDA material layer that has been ethylene oxide (ETO) sterilized. This data shows that, following ETO sterilization, glucose sensor comprising an HDA material layer exhibit excellent ability to sense glucose in-vivo sensor over at least 11 days of wear.

FIG. 5 shows data from an in vivo study monitoring glucose in pigs using a amperometric glucose sensor comprising an HDA material layer that has been ethylene oxide (ETO) sterilized following such ETO sterilization parameters. This data shows that, following ETO sterilization, glucose sensor comprising an HDA material layer exhibit excellent ability to sense glucose in-vivo sensor over at least 11 days of wear.

Yet another embodiment of the invention is a method of sensing glucose concentrations in a fluid (e.g. an environment where the concentrations of glucose are low relative to the concentrations of oxygen) comprising disposing an electrochemical glucose sensor in the fluid, wherein the electrochemical glucose sensor comprises a base layer; a working electrode disposed on the base layer; and a multilayer analyte sensor stack disposed on the working electrode. In these embodiments, the multilayer analyte sensor stack comprises an analyte sensing layer comprising glucose oxidase disposed over the working electrode, wherein the analyte sensing layer detectably alters the electrical current at the working electrode in the presence of an analyte. This stack also includes a high-density amine layer, for example one comprising poly-l-lysine polymers, wherein the high-density amine layer is disposed over the analyte sensing layer; and an analyte modulating layer disposed over this high-density amine layer, wherein the analyte modulating layer modulates the diffusion of glucose therethrough. These methods further comprise monitoring fluctuations in electrical conductivity that can be observed when glucose reacts with glucose oxidase; and correlating the fluctuations in electrical conductivity with a concentration of glucose so that glucose concentrations in the fluid are sensed. In such embodiments, the high-density amine layer functions to increase adhesion between the layers of the multilayer analyte sensor stack while simultaneously decreasing sensor signal changes that result from fluctuating levels of oxygen ($O_2$) as glucose concentrations in the fluid are sensed. Optionally, the analyte modulating layer is a glucose limiting membrane that comprises a polyurethane/polyurea polymer formed from a mixture comprising a diisocyanate, a hydrophilic polymer comprising a hydrophilic diol or hydrophilic diamine, and a siloxane having an amino, hydroxyl or carboxylic acid functional group at a terminus.

In typical embodiments of the invention, electrochemical sensors are operatively coupled to a sensor input capable of receiving signals from the electrochemical sensor; and a processor coupled to the sensor input, wherein the processor is capable of characterizing one or more signals received from the electrochemical sensor. In certain embodiments of the invention, the electrical conduit of the electrode is coupled to a potentiostat (see, e.g. FIG. 4). Optionally, a pulsed voltage is used to obtain a signal from an electrode. In typical embodiments of the invention, the processor is capable of comparing a first signal received from a working electrode in response to a first working potential with a second signal received from a working electrode in response to a second working potential. Optionally, the electrode is coupled to a processor adapted to convert data obtained from observing fluctuations in electrical current from a first format into a second format. Such embodiments include, for example, processors designed to convert a sensor current Input Signal (e.g. ISIG measured in nA) to a blood glucose concentration.

In many embodiments of the invention, the sensors comprise a biocompatible region adapted to be implanted in vivo. In some embodiments, the sensor comprises a discreet probe that pierces an in vivo environment. In embodiments of the invention, the biocompatible region can comprise a polymer that contacts an in vivo tissue. Optionally, the polymer is a hydrophilic polymer (e.g. one that absorbs water). In this way, sensors used in the systems of the invention can be used to sense a wide variety of analytes in different aqueous environments. In some embodiments of the invention, the electrode is coupled to a piercing member (e.g. a needle) adapted to be implanted in vivo. While sensor embodiments of the invention can comprise one or two piercing members, optionally such sensor apparatuses can include 3 or 4 or 5 or more piercing members that are coupled to and extend from a base element and are operatively coupled to 3 or 4 or 5 or more electrochemical sensors (e.g. microneedle arrays, embodiments of which are disclosed for example in U.S. Pat. Nos. 7,291,497 and 7,027,478, and U.S. patent Application No. 20080015494, the contents of which are incorporated by reference).

In some embodiments of the invention, the apparatus comprises one or more working electrodes, counter electrodes and reference electrodes, optionally clustered together in units consisting essentially of one working electrode, one counter electrode and one reference electrode; and the clustered units are longitudinally distributed on the base layer in a repeating pattern of units. In some sensor embodiments, the distributed electrodes are organized/disposed within a flex-circuit assembly (i.e. a circuitry assembly that utilizes flexible rather than rigid materials). Such flex-circuit assembly embodiments provide an interconnected assembly of elements (e.g. electrodes, electrical conduits, contact pads and the like) configured to facilitate wearer comfort (for example by reducing pad stiffness and wearer discomfort).

As noted above, the sensor electrodes of the invention are coated with a plurality of materials having properties that, for example, facilitate analyte sensing. In typical embodiments of the invention, an analyte sensing layer is disposed directly on a working electrode, and includes an agent that is selected for its ability to detectably alter the electrical current at the working electrode in the presence of an analyte. In the working embodiments of the invention that are disclosed herein, the agent is glucose oxidase, a protein that undergoes a chemical reaction in the presence of glucose that results in an alteration in the electrical current at the working electrode. These working embodiments further include an analyte modulating layer disposed over the analyte sensing layer, wherein the analyte modulating layer modulates the diffusion of glucose as it migrates from an in vivo environment to the analyte sensing layer. In certain embodiments of the invention, the analyte modulating layer comprises a hydrophilic comb-copolymer having a central chain and a plurality of side chains coupled to the central chain, wherein at least one side chain comprises a silicone moiety. In certain embodiments of the invention, the analyte modulating layer comprises a blended mixture of: a linear polyurethane/polyurea polymer, and a branched acrylate polymer; and the linear polyurethane/polyurea polymer and the branched acrylate polymer are blended at a ratio of between 1:1 and 1:20 (e.g. 1:2) by weight %. Typically, this analyte modulating layer composition comprises a first polymer formed from a mixture comprising a diisocyanate; at least one hydrophilic diol or hydrophilic diamine; and a siloxane; that is blended with a second polymer formed from a mixture comprising: a 2-(dimethylamino)ethyl methacrylate; a methyl methacrylate; a polydimethyl siloxane monomethacryloxypropyl; a poly(ethylene oxide) methyl ether methacrylate; and a 2-hydroxyethyl methacrylate. As disclosed herein, additional material layers can be included in such apparatuses. For example, in typical embodiments of the invention, the apparatus comprises a high-density amine layer which is disposed between and in direct contact with the analyte sensing layer and the analyte modulating layer so as to exhibit a number of beneficial properties including an ability to provide a smoother surface structure and further promote adhesion between the analyte sensing layer and the analyte modulating layer. Without being bound by a specific scientific theory or mechanism of action, it is believed that adhesion between layers is promoted by smoother layer contact architectures as well as Vander Waals force interactions between the HDA polymers in the HDA layer and compounds present in the analyte sensing layer that is disposed on a first side of this HDA layer, and Vander Waals force interactions between the HDA polymers and compounds present in the analyte modulating layer that is disposed on a second side of this HDA layer (i.e. so that the HDA layer is in a "sandwich" configuration).

Figure 2B:
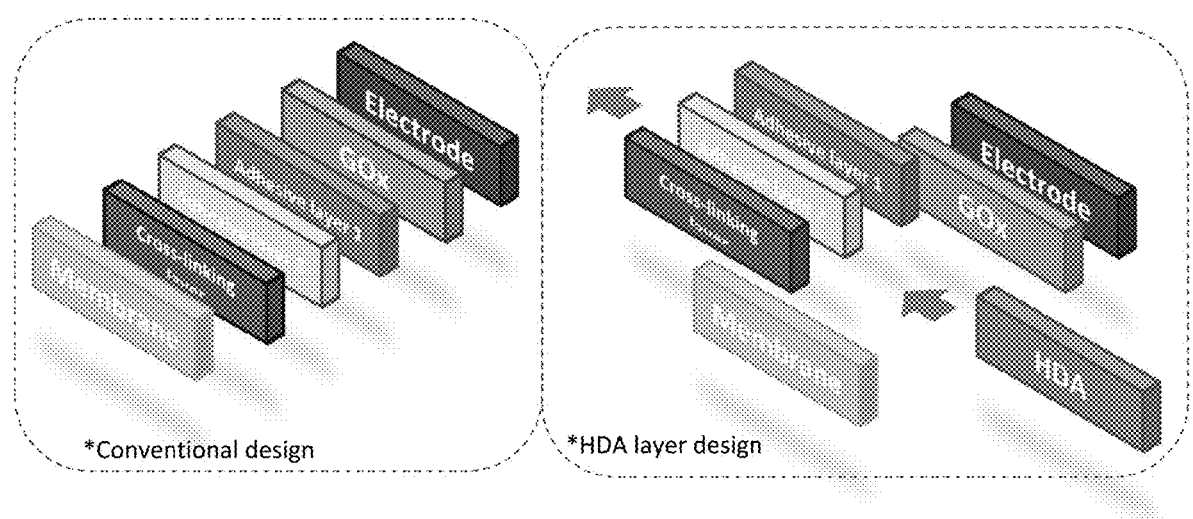
FIG. 2B provides a schematic showing differences between such conventional multilayer sensor stacks and the novel sensor stacks that are disclosed herein (i.e. sensor stacks that do not comprise a layer that includes glutaraldehyde, a layer that includes serum albumin, or a layer that includes a siloxane adhesion promoter).

One prior art conventional sensor embodiment shown in FIG. 2A is a amperometric sensor 100 having a plurality of layered elements including a base layer 102, a conductive layer 104 (e.g. one comprising the plurality of electrically conductive members) which is disposed on and/or combined with the base layer 102. The following comments relate to this conventional sensor which is described to help understand the differences between such conventional sensors and the invention disclosed herein. Typically, the conductive layer 104 comprises one or more electrodes. An analyte sensing layer 110 (typically comprising an enzyme such as glucose oxidase) is disposed on one or more of the exposed electrodes of the conductive layer 104. A protein layer 116 disposed upon the analyte sensing layer 110. An analyte modulating layer 112 is disposed above the analyte sensing layer 110 to regulate analyte (e.g. glucose) access with the analyte sensing layer 110. An adhesion promoter layer 114 is disposed between layers such as the analyte modulating layer 112 and the analyte sensing layer 110 as shown in FIG. 2A in order to facilitate their contact and/or adhesion. This embodiment also comprises a cover layer 106 such as a polymer coating can be disposed on portions of the sensor 100. Apertures 108 can be formed in one or more layers of such sensors. Amperometric glucose sensors having this type of design are disclosed, for example, in U.S. Patent Application Publication Nos. 20070227907, 20100025238, 20110319734 and 20110152654, the contents of each of which are incorporated herein by reference. FIG. 2B shows a comparison between these conventional multilayer sensor stacks and the invention disclosed herein (i.e. ones comprising a HDA layer 500).

As noted above, embodiments of the invention also include methods for making and using the HDA multilayer sensor stacks disclosed herein. Yet another embodiment of the invention is a method of sensing an analyte within the body of a mammal. Typically, this method comprises implanting an analyte sensor having an HDA multilayer sensor stack within the mammal (e.g. in the interstitial space of a diabetic individual), sensing an alteration in current at the working electrode in the presence of the analyte; and then correlating the alteration in current with the presence of the analyte, so that the analyte is sensed.

Embodiments of the invention also provide articles of manufacture and kits for observing a concentration of an analyte. In an illustrative embodiment, the kit includes a sensor comprising a HDA multilayer sensor stack as discussed herein. In typical embodiments, the sensors are disposed in the kit within a sealed sterile dry package. Optionally the kit comprises an insertion device that facilitates insertion of the sensor. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. The kit and/or sensor set may include other materials desirable from a commercial and user standpoint, including buffers, diluents, filters, needles, syringes, and package inserts with instructions for use.

Specific aspects of embodiments of the invention are discussed in detail in the following sections.
Typical Elements, Configurations and Analyte Sensor Embodiments of the Invention A. Typical Elements Found in of Embodiments of the Invention The invention disclosed herein includes compositions comprising high-density amine (HDA) polymers, compositions which can be used in layered electrochemical sensor stacks as a way to impart functional benefits to the sensors. FIG. 1 provides a schematic that illustrates the general structures of such polymers can be used to make these polymers.

FIG. 2A illustrates a cross-section of a conventional sensor embodiment 100. The components of the sensor are typically characterized herein as layers in this layered electrochemical sensor stack because, for example, it allows for a facile characterization of conventional sensor structures such as those shown in FIG. 2A and their differences from the invention disclosed herein as shown in FIG. 2B (i.e. ones comprising a HDA layer 500). Artisans will understand, that in certain embodiments of the invention, the sensor constituents are combined such that multiple constituents form one or more heterogeneous layers. In this context, those of skill in the art understand that, while certain layers/components of conventional sensor embodiments are useful in the HDA sensors disclosed herein, the placement and composition of the layered constituents is very different in HDA sensor embodiments of the invention. Those of skill in this art will understand that certain embodiments if the invention include elements/layers that are found in conventional sensors while others are excluded, and/or new material layers/elements are included. For example, certain elements disclosed in FIG. 2A are also found in the invention disclosed herein (e.g. a base, analyte sensing layer, an analyte modulating layer etc.) while, as shown in FIG. 2B, other elements are not (e.g. separate HSA protein layers, layers comprising a siloxane adhesion promoter etc.). Similarly, embodiments of the invention include layers/elements having materials disposed in unique configurations that are not found in conventional sensors (e.g. high-density amine (HDA) polymer layers 500).

The conventional embodiment shown in FIG. 2A includes a base layer 102 to support the sensor 100. The base layer 102 can be made of a material such as a metal and/or a ceramic and/or a polymeric substrate, which may be self-supporting or further supported by another material as is known in the art. Embodiments can include a conductive layer 104 which is disposed on and/or combined with the base layer 102. Typically, the conductive layer 104 comprises one or more electrically conductive elements that function as electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the conventional sensor configuration shown in FIG. 2A, an analyte sensing layer 110 is disposed on one or more of the exposed electrodes of the conductive layer 104. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic Diabetes.

In embodiments of the invention, the analyte sensing layer 110 can be applied over portions of the conductive layer or over the entire region of the conductive layer. Typically, the analyte sensing layer 110 is disposed on the working electrode which can be the anode or the cathode. Optionally, the analyte sensing layer 110 is also disposed on a counter and/or reference electrode. Methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like.

In this context, a variety of pin coating materials and methods are known in the art (see, e.g. Sahu et al., Indian J. Phys. 83 (4) 493-502 (2009), and U.S. Patent Publications 20020127878, 20020127878, 20090285982 and 20140272704). In certain embodiments of the invention, the material of the high-density amine layer comprising polymers having a plurality of repeating amine groups (e.g. poly-l-lysine polymers) is blended with another material such as a solvent or other agent that modulates solution viscosity in order to optimize spin coating uniformity. In this context, to prepare an HDA layer for spin coating, one can mix a viscosity modulating agent and/or one or two or more solvents together. For example, with two solvents one can use a major component of something that evaporates relatively quickly and a minor component of something that is relatively slow to evaporate. By using this combination, it is often possible to optimize aspects of this process in that during the spin coating process the major component evaporates quickly to give good coverage and a uniform thick film, and the remaining minor component still leaves enough plasticity for the molecules to organize before the film is completely dry.

The analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In typical embodiments of the invention, a layer of materials comprising a high-density amine composition layer 500 is disposed between the analyte modulating layer 112 and the analyte sensing layer 110 as shown in FIG. 2B in order to facilitate their contact and/or adhesion. In typical embodiments of the invention, the high-density amine layer 500 comprises a first side in direct contact with the analyte sensing layer, and a second side in direct contact with the analyte modulating layer and functions as an adhesive layer that binds the analyte sensing layer to the analyte modulating layer. Optionally, the analyte sensing layer comprises glucose oxidase disposed in the layer so that the analyte sensor senses glucose; and the high-density amine layer 500 further functions to decrease sensor signal changes that result from fluctuating levels of oxygen ($O_2$). In certain embodiments of the invention, the poly-l-lysine in the high-density amine layer 500 has molecular weights between 30 KDa and 300 KDa, for example, molecular weights between 150 KDa and 300 KDa. Typically, the poly-l-lysine in the high-density amine layer 500 is in amounts from 0.1 weight-to-weight percent to 0.5 weight-to-weight percent. Optionally, the high-density amine layer 500 is from 0.1 to 0.4 microns thick.

Typical Analyte Sensor Constituents of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that selected elements from these thin film analyte sensors can be adapted for use in a number of sensor systems such as those described herein.

Base Constituent

Sensors of the invention typically include a base constituent (see, e.g. element 102 in FIG. 2A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

Conductive Constituent

The electrochemical sensors of the invention typically include a conductive constituent disposed upon the base constituent that includes at least one electrode for contacting an analyte or its byproduct (e.g. oxygen and/or hydrogen peroxide) to be assayed (see, e.g. element 104 in FIG. 2A). The term "conductive constituent" is used herein according to art accepted terminology. An illustrative example of this is a conductive constituent that forms a working electrode that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1× reference electrode, a 2.6× working electrode and a 3.6× counter electrode.

Analyte Sensing Constituent

The electrochemical sensors of the invention include an analyte sensing constituent disposed on the electrodes of the sensor (see, e.g. element 110 in FIG. 2A). The term "analyte sensing constituent" is used herein according to art accepted terminology and refers to a constituent comprising a material that is capable of recognizing or reacting with an analyte whose presence is to be detected by the analyte sensor apparatus. Typically, this material in the analyte sensing constituent produces a detectable signal after interacting with the analyte to be sensed, typically via the electrodes of the conductive constituent. In this regard, the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Some sensor embodiments of this element of the invention utilize an enzyme (e.g. glucose oxidase) that optionally has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide.

As noted above, the enzyme and the second protein (e.g. an albumin) can be treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture (however in certain embodiments of the invention disclosed herein, glutaraldehyde is excluded because the addition of a cross-linking reagent to the protein mixture creates a less active protein paste).

Alternative embodiments of analyte sensing constituents are not formed using glutaraldehyde, and are instead formed to include entrapped and/or crosslinked polypeptides such as glucose oxidase crosslinked to polyvinyl alcohol (PVA, see, e.g. CAS number 9002-89-5) polymers. As is known in the art, polyvinyl alcohol reacts with aldehydes to form water insoluble polyacetals. In a pure PVA medium having a pH around 5.0, polymer reaction with dialdehydes is expected to form an acetal cross-linked structure. In certain embodiments of the invention, such crosslinking reactions can be performed using a chemical vapor deposition (CVD) process. Due to the acidity of the PVA polymer solution, crosslinking reactions in CVD systems are simple and routine. Moreover, acidic conditions can be created by introducing compounds such as acetic acid into glutaraldehyde solutions, so a CVD system can provide an acid vapor condition. In addition the pH of the polymer medium can be adjusted by adding acidic compounds such as citric acid, polymer additives such as polylysine, HBr and the like.

Embodiments of the analyte sensing constituents include compositions having properties that make them particularly well suited for use in ambulatory glucose sensors of the type worn by diabetic individuals. Such embodiments of the invention include PVA-SbQ compositions for use in layered analyte sensor structures that comprise between 1 mol % and 12.5 mol % SbQ. In certain embodiments of the invention that are adapted or use in glucose sensors, the constituents in this layer are selected so that the molecular weight of the polyvinyl alcohol is between 30 kilodaltons and 150 kilodaltons and the SbQ in the polyvinyl alcohol is present in an amount between 1 mol % and 4 mol %. In some embodiments of the invention the analyte sensing layer is formed to comprise from 5% to 12% PVA by weight. In some embodiments of the invention the analyte sensing layer is formed to comprise glucose oxidase in an amount from 10 KU/mL to 20 KU/mL.

Embodiments of the analyte sensing constituents include analyte sensing layers selected for their ability to provide desirable characteristics for implantable sensors. In certain embodiments of the invention an amount or ratio of PVA within the composition is used to modulate the water adsorption of the composition, the crosslinking density of the composition etc. Such formulations can readily be evaluated for their effects on phenomena such as $H_2O$ adsorption, sensor isig drift and in vivo start up profiles. Sufficient $H_2O$ adsorption can help to maintain a normal chemical and electrochemical reaction within amperometric analyte sensors. Consequently, it is desirable to form such sensors from compositions having an appropriate hydrophilic chemistry. In this context, the PVA-GOx compositions disclosed herein can be used to create electrolyte hydrogels that are useful in internal coating/membrane layers and can also be coated on top of an analyte modulating layer (e.g. a glucose limiting membrane or "GLM") in order to improve the biocompatibility and hydrophilicity of the GLM layer.

As noted above, in some embodiments of the invention, the analyte sensing constituent includes an agent (e.g. glucose oxidase) capable of producing a signal (e.g. a change in oxygen and/or hydrogen peroxide concentrations) that can be sensed by the electrically conductive elements (e.g. electrodes which sense changes in oxygen and/or hydrogen peroxide concentrations). However, other useful analyte sensing constituents can be formed from any composition that is capable of producing a detectable signal that can be sensed by the electrically conductive elements after interacting with a target analyte whose presence is to be detected. In some embodiments, the composition comprises an enzyme that modulates hydrogen peroxide concentrations upon reaction with an analyte to be sensed. Alternatively, the composition comprises an enzyme that modulates oxygen concentrations upon reaction with an analyte to be sensed. In this context, a wide variety of enzymes that either use or produce hydrogen peroxide and/or oxygen in a reaction with a physiological analyte are known in the art and these enzymes can be readily incorporated into the analyte sensing constituent composition. A variety of other enzymes known in the art can produce and/or utilize compounds whose modulation can be detected by electrically conductive elements such as the electrodes that are incorporated into the sensor designs described herein. Such enzymes include for example, enzymes specifically described in Table 1, pages 15-29 and/or Table 18, pages 111-112 of Protein Immobilization: Fundamentals and Applications (Bioprocess Technology, Vol 14) by Richard F. Taylor (Editor) Publisher: Marcel Dekker; Jan. 7, 1991) the entire contents of which are incorporated herein by reference.

High-Density Amine Constituent

The electrochemical sensors of the invention include one or more high-density amine constituent layers (see, e.g. element 500 in FIG. 2B) that provide the sensors with a number of beneficial functions. Such layers can optimize sensor function, for example by acting as an adhesion promoting constituent for layers adjacent to the HDA layer, by decreasing fluctuations that can occur in glucose oxidase based sensors in the presence of fluctuating concentration of oxygen, by improving sensor initialization profiles and the like. The term "adhesion promoting constituent" is used herein according to art accepted terminology and refers to a constituent that includes materials selected for their ability to promote adhesion between adjoining constituents in the sensor. Typically, the high-density amine adhesion promoting constituent is disposed between and in direct contact with the analyte sensing constituent and the analyte modulating constituent. In typical embodiments, the high-density amine layer 500 comprises poly-l-lysine having molecular weights between 30 KDa and 300 KDa (e.g. between 150 KDa and 300 KDa). The concentrations of poly-l-lysine in such high-density amine layers 500 is typically from 0.1 weight-to-weight percent to 0.5 weight-to-weight percent and the high-density amine layer 500 is from 0.1 to 0.4 microns thick. In embodiments where the analyte sensing layer comprises glucose oxidase so that the analyte sensor senses glucose, and the high-density amine layer 500 functions to decrease sensor signal changes that result from fluctuating levels of oxygen ($O_2$).

Analyte Modulating Constituent

The electrochemical sensors of the invention include an analyte modulating constituent disposed on the sensor (see, e.g. element 112 in FIG. 2A). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferants, such as ascorbic acid and uric acid, diffuse through a primary membrane of the sensor. As the glucose, oxygen and interferants reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The analyte modulating sensor membrane assembly serves several functions, including selectively allowing the passage of glucose therethrough (see, e.g. U.S. Patent Application No. 2011-0152654).

C. Typical Analyte Sensor System Embodiments of the Invention

Embodiments of the sensor elements and sensors can be operatively coupled to a variety of other system elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Figure 4:
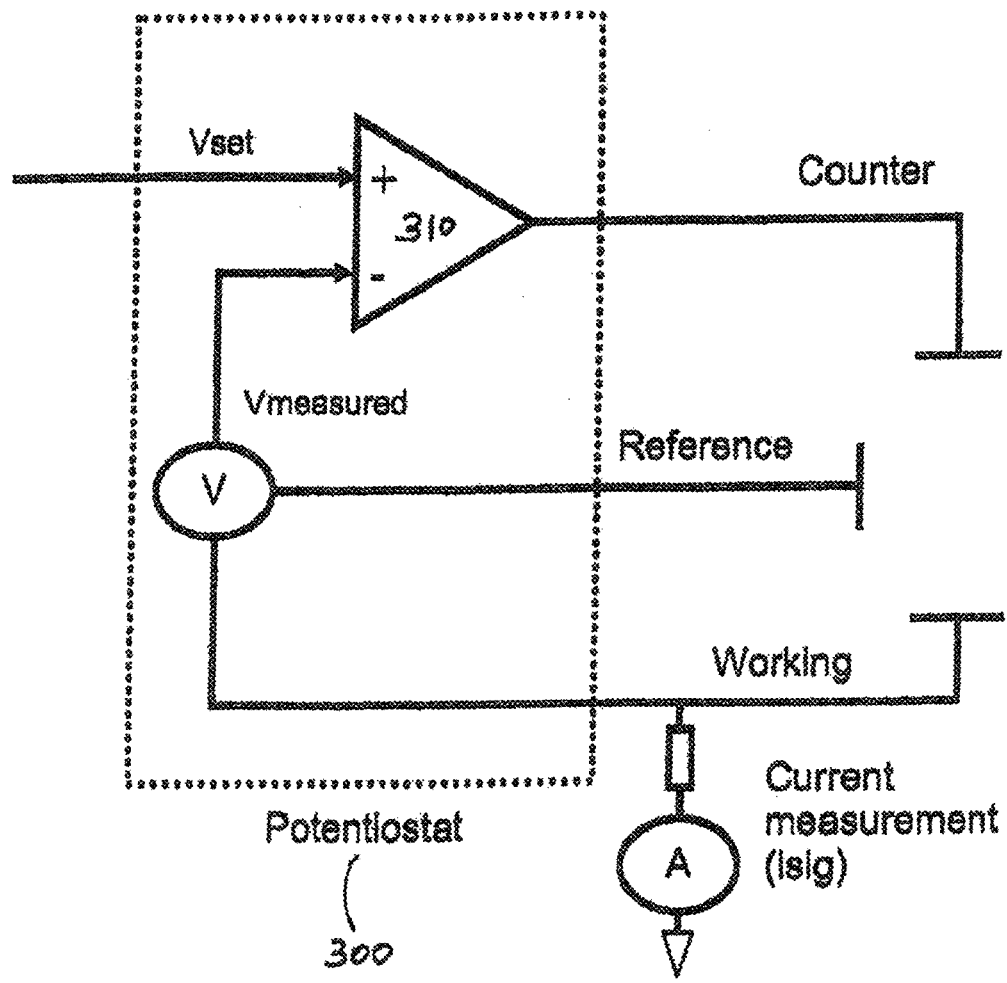
FIG. 4 shows a schematic of a potentiostat that may be used to measure current in embodiments of the present invention.

FIG. 4 shows a schematic of a potentiostat that may be used to measure current in embodiments of the present invention. As shown in FIG. 4, a potentiostat 300 may include an op amp 310 that is connected in an electrical circuit so as to have two inputs: Vset and Vmeasured. As shown, Vmeasured is the measured value of the voltage between a reference electrode and a working electrode. Vset, on the other hand, is the optimally desired voltage across the working and reference electrodes. The current between the counter and reference electrode is measured, creating a current measurement (isig) that is output from the potentiostat.

Embodiments of the invention include devices which process display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver every 5 minutes to provide providing real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include for example the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically, in such devices, the physiological characteristic values include a plurality of measurements of blood glucose.

Figure 3:
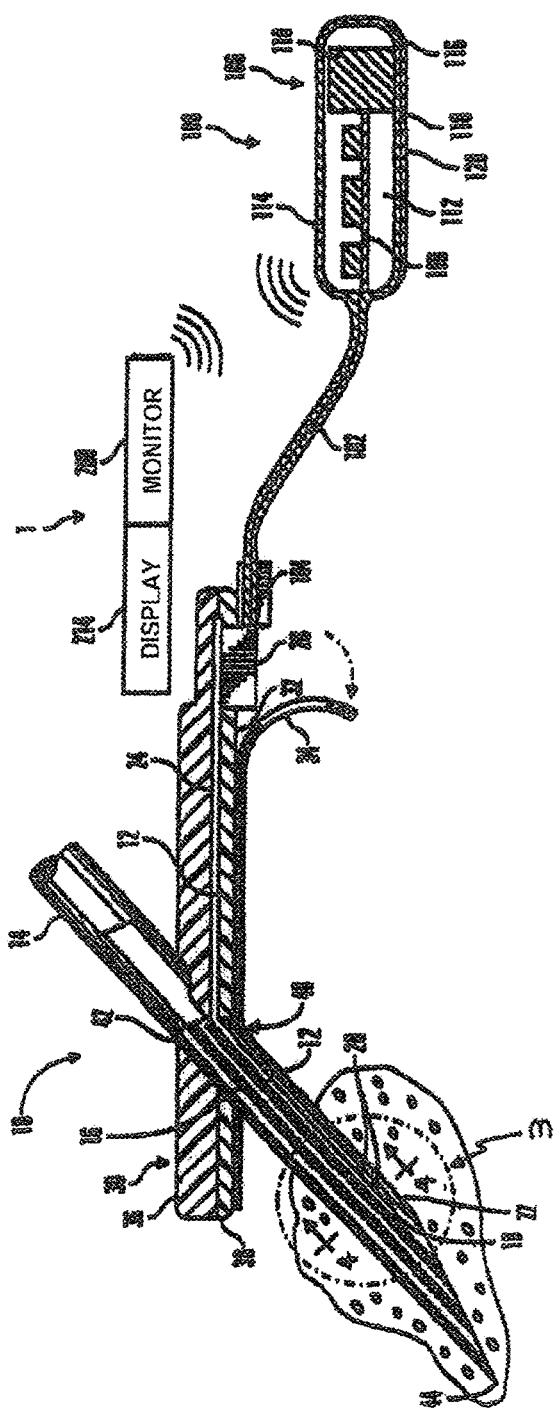
FIG. 3 provides a perspective view illustrating a subcutaneous sensor insertion set, a telemetered characteristic monitor transmitter device, and a data receiving device embodying features of the invention.

FIG. 3 provides a perspective view of one generalized embodiment of subcutaneous sensor insertion system and a block diagram of a sensor electronics device according to one illustrative embodiment of the invention. Additional elements typically used with such sensor system embodiments are disclosed for example in U.S. Patent Application No. 20070163894, the contents of which are incorporated by reference. FIG. 3 provides a perspective view of a telemetered characteristic monitor system 1, including a subcutaneous sensor set 10 provided for subcutaneous placement of an active portion of a flexible sensor 12, or the like, at a selected site in the body of a user. The subcutaneous or percutaneous portion of the sensor set 10 includes a hollow, slotted insertion needle 14 having a sharpened tip 44, and a cannula 16. Inside the cannula 16 is a sensing portion 18 of the sensor 12 to expose one or more sensor electrodes 20 to the user's bodily fluids through a window 22 formed in the cannula 16. The sensing portion 18 is joined to a connection portion 24 that terminates in conductive contact pads, or the like, which are also exposed through one of the insulative layers. The connection portion 24 and the contact pads are generally adapted for a direct wired electrical connection to a suitable monitor 200 coupled to a display 214 for monitoring a user's condition in response to signals derived from the sensor electrodes 20. The connection portion 24 may be conveniently connected electrically to the monitor 200 or a characteristic monitor transmitter 100 by a connector block 28 (or the like).

As shown in FIG. 3, in accordance with embodiments of the present invention, subcutaneous sensor set 10 may be configured or formed to work with either a wired or a wireless characteristic monitor system. The proximal part of the sensor 12 is mounted in a mounting base 30 adapted for placement onto the skin of a user. The mounting base 30 can be a pad having an underside surface coated with a suitable pressure sensitive adhesive layer 32, with a peel-off paper strip 34 normally provided to cover and protect the adhesive layer 32, until the sensor set 10 is ready for use. The mounting base 30 includes upper and lower layers 36 and 38, with the connection portion 24 of the flexible sensor 12 being sandwiched between the layers 36 and 38. The connection portion 24 has a forward section joined to the active sensing portion 18 of the sensor 12, which is folded angularly to extend downwardly through a bore 40 formed in the lower base layer 38. Optionally, the adhesive layer 32 (or another portion of the apparatus in contact with in vivo tissue) includes an anti-inflammatory agent to reduce an inflammatory response and/or anti-bacterial agent to reduce the chance of infection. The insertion needle 14 is adapted for slide-fit reception through a needle port 42 formed in the upper base layer 36 and through the lower bore 40 in the lower base layer 38. After insertion, the insertion needle 14 is withdrawn to leave the cannula 16 with the sensing portion 18 and the sensor electrodes 20 in place at the selected insertion site. In this embodiment, the telemetered characteristic monitor transmitter 100 is coupled to a sensor set 10 by a cable 102 through a connector 104 that is electrically coupled to the connector block 28 of the connector portion 24 of the sensor set 10.

In the embodiment shown in FIG. 3, the telemetered characteristic monitor 100 includes a housing 106 that supports a printed circuit board 108, batteries 110, antenna 112, and the cable 102 with the connector 104. In some embodiments, the housing 106 is formed from an upper case 114 and a lower case 116 that are sealed with an ultrasonic weld to form a waterproof (or resistant) seal to permit cleaning by immersion (or swabbing) with water, cleaners, alcohol or the like. In some embodiments, the upper and lower case 114 and 116 are formed from a medical grade plastic. However, in alternative embodiments, the upper case 114 and lower case 116 may be connected together by other methods, such as snap fits, sealing rings, RTV (silicone sealant) and bonded together, or the like, or formed from other materials, such as metal, composites, ceramics, or the like. In other embodiments, the separate case can be eliminated and the assembly is simply potted in epoxy or other moldable materials that is compatible with the electronics and reasonably moisture resistant. As shown, the lower case 116 may have an underside surface coated with a suitable pressure sensitive adhesive layer 118, with a peel-off paper strip 120 normally provided to cover and protect the adhesive layer 118, until the sensor set telemetered characteristic monitor transmitter 100 is ready for use.

In the illustrative embodiment shown in FIG. 3, the subcutaneous sensor set 10 facilitates accurate placement of a flexible thin film electrochemical sensor 12 of the type used for monitoring specific blood parameters representative of a user's condition. The sensor 12 monitors glucose levels in the body, and may be used in conjunction with automated or semi-automated medication infusion pumps of the external or implantable type as described in U.S. Pat. Nos. 4,562,751; 4,678,408; 4,685,903 or 4,573,994, to control delivery of insulin to a diabetic patient.

In the illustrative embodiment shown in FIG. 3, the sensor electrodes 10 may be used in a variety of sensing applications and may be configured in a variety of ways. For example, the sensor electrodes 10 may be used in physiological parameter sensing applications in which some type of biomolecule is used as a catalytic agent. For example, the sensor electrodes 10 may be used in a glucose and oxygen sensor having a glucose oxidase enzyme catalyzing a reaction with the sensor electrodes 20. The sensor electrodes 10, along with a biomolecule or some other catalytic agent, may be placed in a human body in a vascular or non-vascular environment. For example, the sensor electrodes 20 and biomolecule may be placed in a vein and be subjected to a blood stream, or may be placed in a subcutaneous or peritoneal region of the human body.

In the embodiment of the invention shown in FIG. 3, the monitor of sensor signals 200 may also be referred to as a sensor electronics device 200. The monitor 200 may include a power source, a sensor interface, processing electronics (i.e. a processor), and data formatting electronics. The monitor 200 may be coupled to the sensor set 10 by a cable 102 through a connector that is electrically coupled to the connector block 28 of the connection portion 24. In an alternative embodiment, the cable may be omitted. In this embodiment of the invention, the monitor 200 may include an appropriate connector for direct connection to the connection portion 104 of the sensor set 10. The sensor set 10 may be modified to have the connector portion 104 positioned at a different location, e.g., on top of the sensor set to facilitate placement of the monitor 200 over the sensor set.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

It is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The invention claimed is:

1. An electrochemical analyte sensor comprising:
    a base layer;
    a working electrode disposed on the base layer; and
    a multilayer analyte sensor stack disposed upon the working electrode comprising:
        (a) an analyte sensing layer disposed directly on the working electrode, wherein the analyte sensing layer detectably alters the electrical current at the working electrode in the presence of an analyte;
        (b) a high-density amine layer disposed over the analyte sensing layer, wherein the high-density amine layer comprises polymers having repeating amine groups; and
        (c) an analyte modulating layer disposed over the high-density amine layer, wherein the analyte modulating layer modulates the diffusion of analyte from an external environment to the working electrode;
    wherein:
    the high-density amine layer comprises a first side in direct contact with the analyte sensing layer or the analyte modulating layer.

2. The electrochemical analyte sensor of claim 1, wherein the multilayer analyte sensor stack does not comprise at least one of:
    a further layer comprising an albumin;
    a further layer comprising a siloxane adhesion promoting agent; or
    a layer comprising glutaraldehyde.

3. The electrochemical analyte sensor of claim 1, wherein the analyte sensing layer comprises glucose oxidase.

4. The electrochemical analyte sensor of claim 1, wherein the multilayer analyte sensor stack consists essentially of (a)-(c).

5. The electrochemical analyte sensor of claim 1, wherein the high-density amine layer functions as an adhesive layer that binds the analyte sensing layer to the analyte modulating layer.

6. The electrochemical analyte sensor of claim 1, wherein the high-density amine layer comprises poly-l-lysine polymers having molecular weights between 30 KDa and 300 KDa.

7. The electrochemical analyte sensor of claim 6, wherein the poly-l-lysine in the high-density amine layer has molecular weights between 150 KDa and 300 KDa.

8. The electrochemical analyte sensor of claim 6, wherein the poly-l-lysine in the high-density amine layer is in amounts from 0.1 weight-to-weight percent to 0.5 weight-to-weight percent.

9. The electrochemical analyte sensor of claim 1, wherein the high-density amine layer is from 0.1 to 0.4 microns thick.

10. The electrochemical analyte sensor of claim 1, wherein the analyte sensing layer comprises glucose oxidase disposed in the layer so that the analyte sensor senses glucose; and the high-density amine layer functions to decrease sensor signal changes that result from fluctuating levels of oxygen ($O_2$).

11. A method of making an electrochemical analyte sensor comprising the steps of:
    disposing a working electrode on a base layer;
    disposing an analyte sensing layer over the working electrode, wherein the analyte sensing layer detectably alters the electrical current at the working electrode in the presence of an analyte;
    disposing a high-density amine layer comprising polymers having repeating amine groups directly on the analyte sensing layer; and
    disposing an analyte modulating layer directly on the high-density amine layer, wherein:
    the analyte modulating layer modulates the diffusion of analyte therethrough; and
    the high-density amine layer is formed to comprise a first side in direct contact with the analyte sensing layer or the analyte modulating layer;
    so that an electrochemical analyte sensor is made.

12. The method of claim 11, the electrochemical sensor comprises a multilayer analyte sensor stack disposed over the working electrode, said multilayer analyte sensor stack consisting essentially of the analyte sensing layer, the high-density amine layer and the analyte modulating layer.

13. The method of claim 12, wherein the analyte sensing layer comprises glucose oxidase disposed in the layer so that the analyte sensor senses glucose; and the high-density amine layer functions to decrease sensor signal changes that result from fluctuating levels of oxygen ($O_2$) during glucose sensing.

14. The method of claim 11, wherein the high-density amine layer is deposited using a spray coating process and the sensor is exposed to an ethylene oxide sterilization process.

15. The method of claim 14, wherein the polymers having repeating amine groups comprise the general structure:

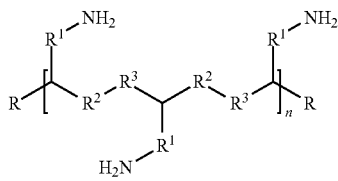

R¹=Alkyl functional groups of various chain lengths (linear and/or branched
R²=Ketone functional group
R³=Nitrogen functional group.

16. A method of sensing glucose concentrations in a fluid comprising:
 (a) disposing an electrochemical glucose sensor in the fluid, wherein the electrochemical glucose sensor comprises:
  a base layer;
  a working electrode disposed on the base layer; and
  a multilayer analyte sensor stack comprising:
   (i) an analyte sensing layer comprising glucose oxidase disposed over the working electrode, wherein the analyte sensing layer detectably alters the electrical current at the working electrode in the presence of an analyte;
   (ii) a high-density amine layer comprising poly-l-lysine polymers, wherein the high-density amine layer is disposed over the analyte sensing layer; and
  (d) an analyte modulating layer disposed over the high-density amine layer, wherein:
   the analyte modulating layer modulates the diffusion of glucose therethrough; and
   the high-density amine layer comprises a first side in direct contact with the analyte sensing layer or the analyte modulating layer;
 (b) monitoring fluctuations in electrical conductivity; and
 (c) correlating the fluctuations in electrical conductivity with a concentration of glucose;
so that glucose concentrations in the fluid are sensed.

17. The method of claim 16, wherein the fluid is interstitial fluid.

18. The method of claim 17, wherein the interstitial fluid is in an individual having diabetes.

19. The method of claim 18, wherein the high-density amine layer functions to decrease sensor signal changes that result from fluctuating levels of oxygen (O2) as glucose concentrations in the fluid are sensed.

20. The method of claim 18, wherein the analyte modulating layer comprises a polyurethane/polyurea polymer formed from a mixture comprising:
 (a) a diisocyanate;
 (b) a hydrophilic polymer comprising a hydrophilic diol or hydrophilic diamine; and
 (c) a siloxane having an amino, hydroxyl or carboxylic acid functional group at a terminus.

* * * * *